United States Patent [19]

Boden et al.

[11] Patent Number: 4,950,495
[45] Date of Patent: Aug. 21, 1990

[54] TETRAHYDRO-5-ISOPROPYL-2-METHYL-2-THIOPHENE ACETONITRILE, ORGANOLEPTIC USES THEREOF AND PROCESS FOR PREPARING SAME

[75] Inventors: Richard M. Boden, Ocean; Joseph A. McGhie, South Orange, both of N.J.

[73] Assignee: International Flavors & Fragrances Inc., New York, N.Y.

[21] Appl. No.: 379,944

[22] Filed: Jul. 14, 1989

Related U.S. Application Data

[62] Division of Ser. No. 273,016, Nov. 18, 1988, Pat. No. 4,883,884.

[51] Int. Cl.$^5$ .............................................. A23L 2/26
[52] U.S. Cl. .................................................... 426/536
[58] Field of Search ........................................ 426/536

[56] References Cited

U.S. PATENT DOCUMENTS 2,425,721  8/1947  Blicke ..................................... 549/74
4,446,076  5/1984  Angeles .................................. 549/74
4,883,844  11/1989  Boden et al. ........................... 549/74

*Primary Examiner*—Alan Siegel
*Attorney, Agent, or Firm*—Arthur L. Liberman

[57] ABSTRACT

Described is the tetrahydro-5-isopropyl-2-methyl-2-thiophene acetonitrile of our invention having the structure:

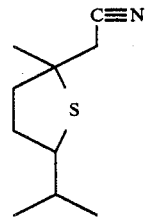

and organoleptic uses thereof in augmenting or enhancing the aroma or taste of perfume compositions, colognes, perfumed articles, foodstuffs and chewing gums.

1 Claim, 5 Drawing Sheets

GLC PROFILE FOR EXAMPLE I.
CRUDE

GLC PROFILE FOR EXAMPLE I. DISTILLATION FRACTION 6.

FIG. 4 IR SPECTRUM FOR EXAMPLE I.

TETRAHYDRO-5-ISOPROPYL-2-METHYL-2-THIOPHENE ACETONITRILE, ORGANOLEPTIC USES THEREOF AND PROCESS FOR PREPARING SAME

This is a divisional of application Ser. No. 273,016, filed 11/18/88 now U.S. Pat. No. 4,883,884.

BACKGROUND OF THE INVENTION

This invention relates to tetrahydro-5-isopropyl-2-methyl-2-thiophene acetonitrile of our invention having the structure:

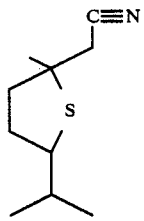

produced by reaction of thioacetic acid with geranonitrile, a mixture of compounds having the structures:

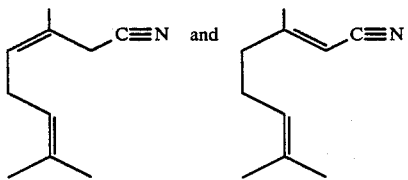

and uses thereof in augmenting or enhancing the aroma or taste of consumable materials including perfume compositions, colognes, perfumed articles, foodstuffs and chewing gums.

There has been considerable work performed relating to substances which can be used to impart (or alter, modify or enhance) fragrances and aromas and/or tastes to (or in) perfume compositions, colognes, perfumed articles, foodstuffs and chewing gums. These substances are used to diminish the use of natural materials, some of which may be in short supply and/or to provide more uniform properties in the finished product.

Powerful, long-lasting, natural buchu leaf, tomato leaf, herbaceous, basil, minty and grapefruit-like aromas with natural "ontiga", tomato leaf, minty and grapefruit-like undertones are highly desirable to many types of perfume compositions, perfumes and perfumed articles, particularly herbal fragrances and herbal fragranced soaps and detergents.

Grapefruit and nootkatone-like aroma and taste nuances are highly desirable in the creation of flavors for foodstuffs and chewing gums.

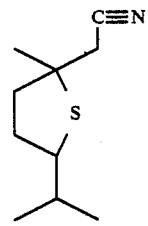

Figure 2:
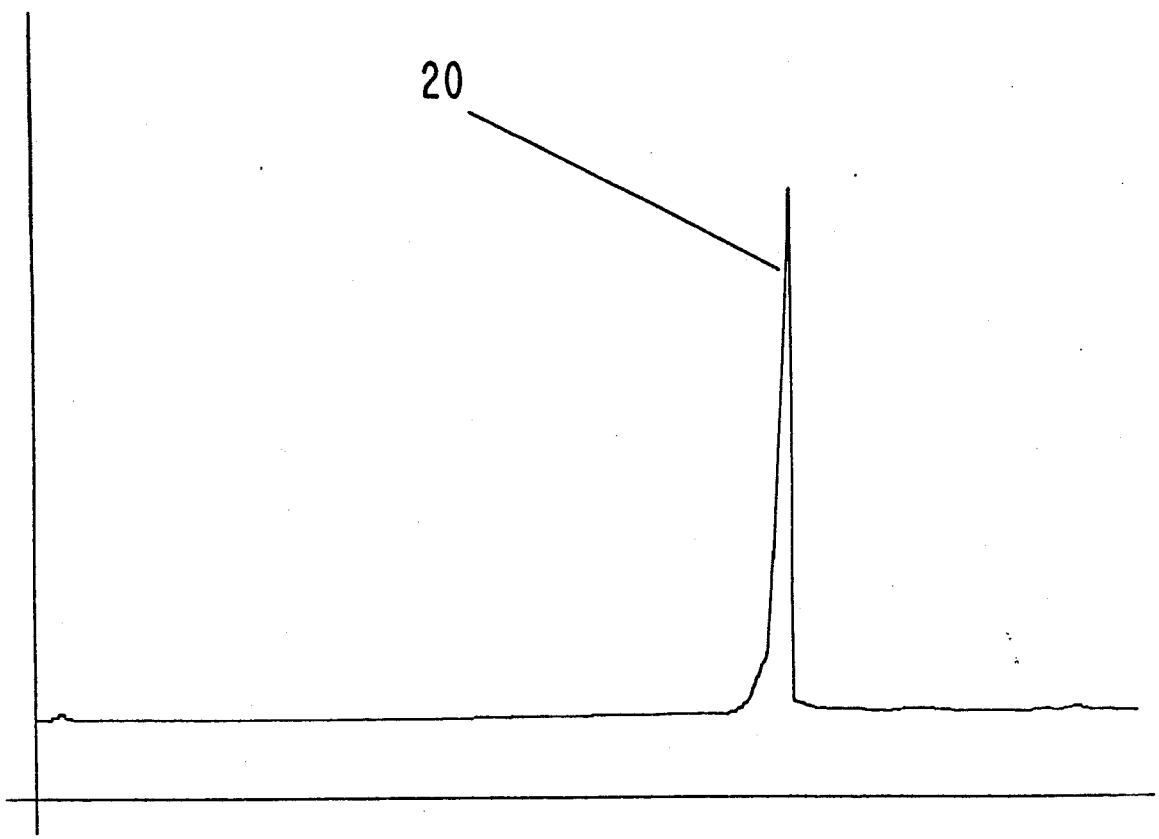

FIG. 2 is the GLC profile for fraction 6 of the distillation of the reaction product of Example I containing the compound having the structure:

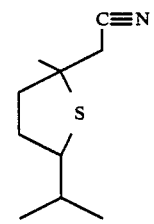

(Conditions: SE-30 column programmed at 100°-220° C. at 8° C. per minute).

Figure 3:
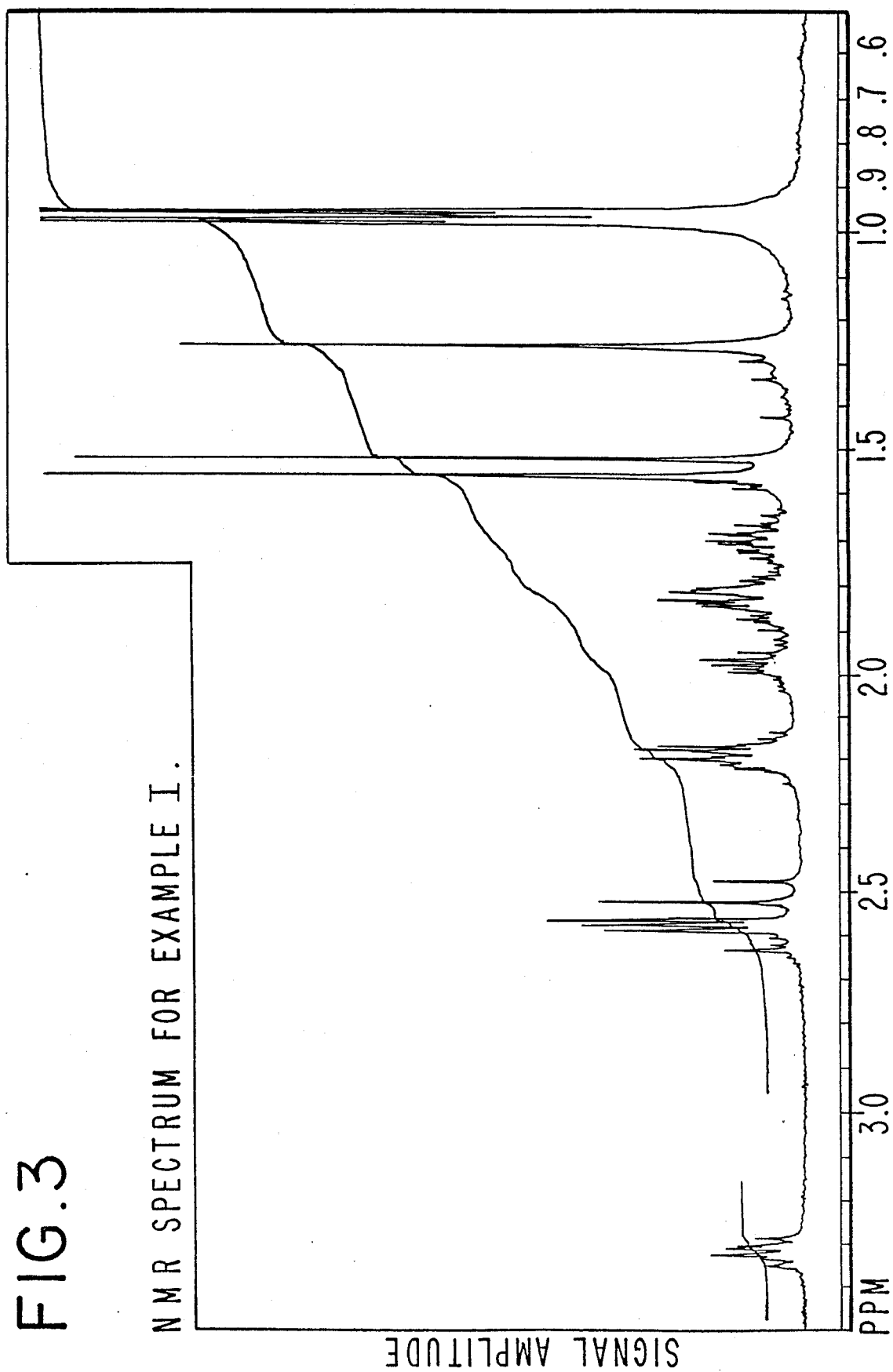

FIG. 3 is the NMR spectrum for the compound having the structure:

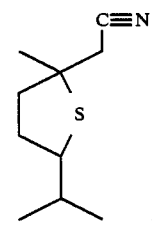

Figure 4:
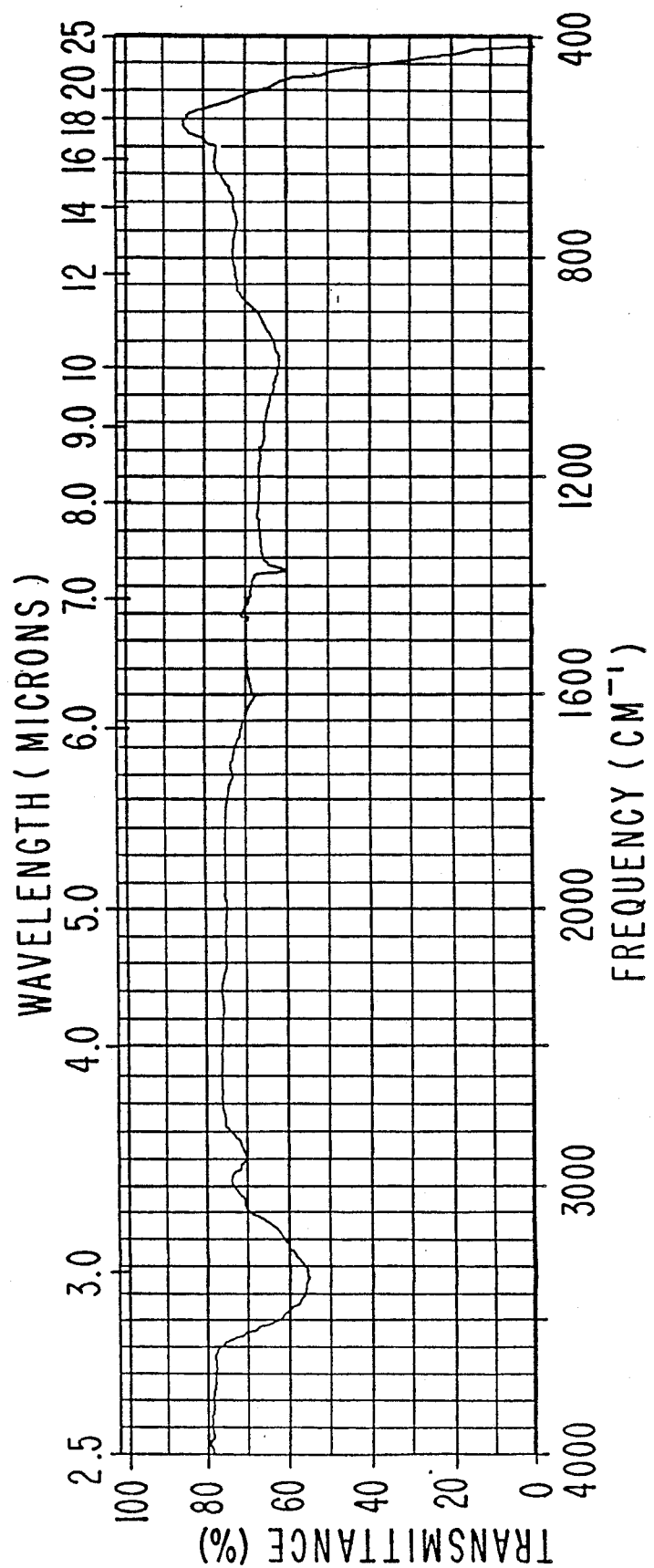

FIG. 4 is the infra-red spectrum for the compound having the structure:

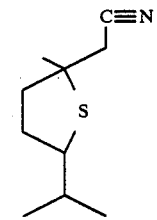

prepared according to Example I.

Figure 5:
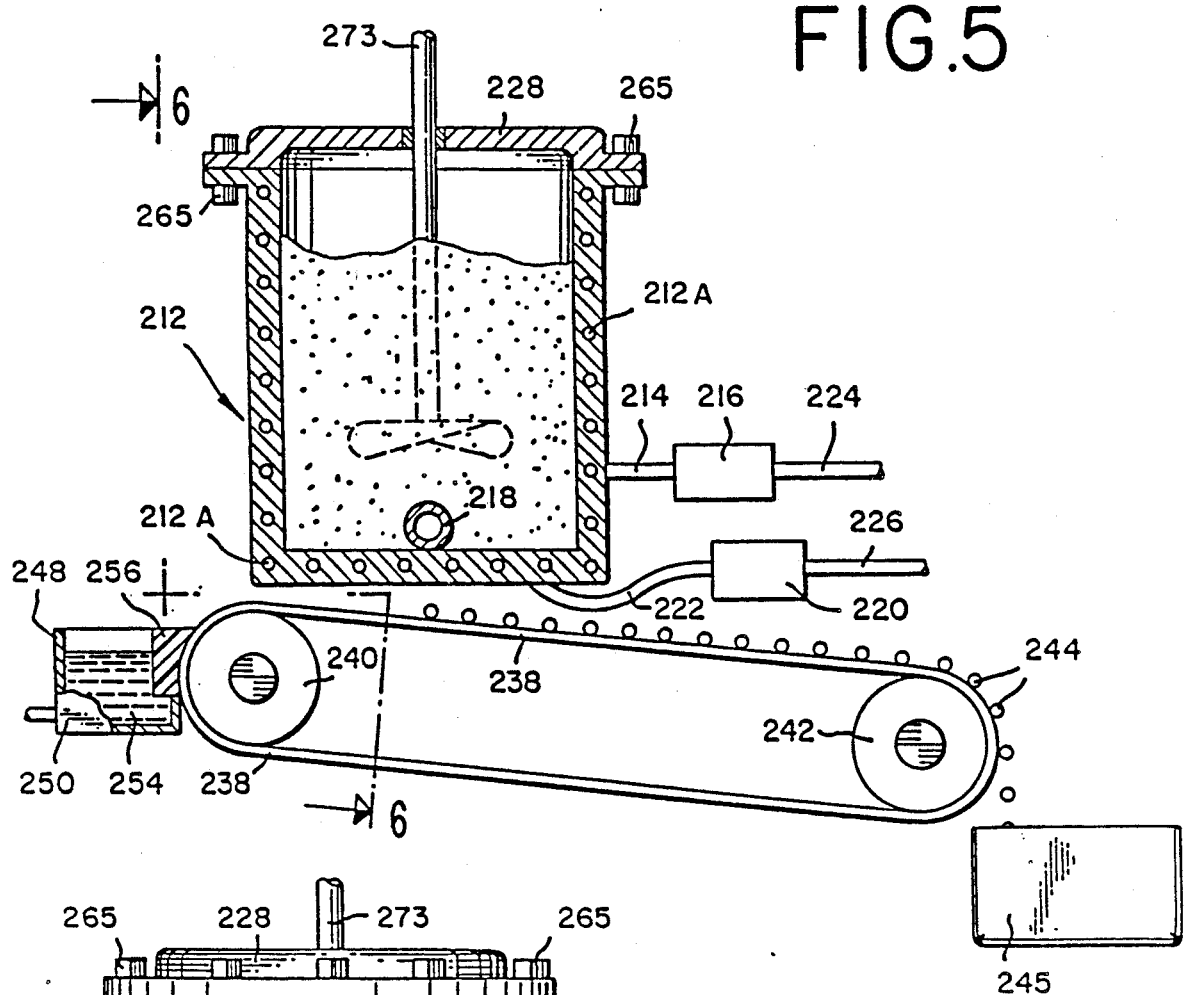

FIG. 5 is a cut-away side elevation view of apparatus used in preparing a fragrance-containing polymer of our invention.

Figure 6:
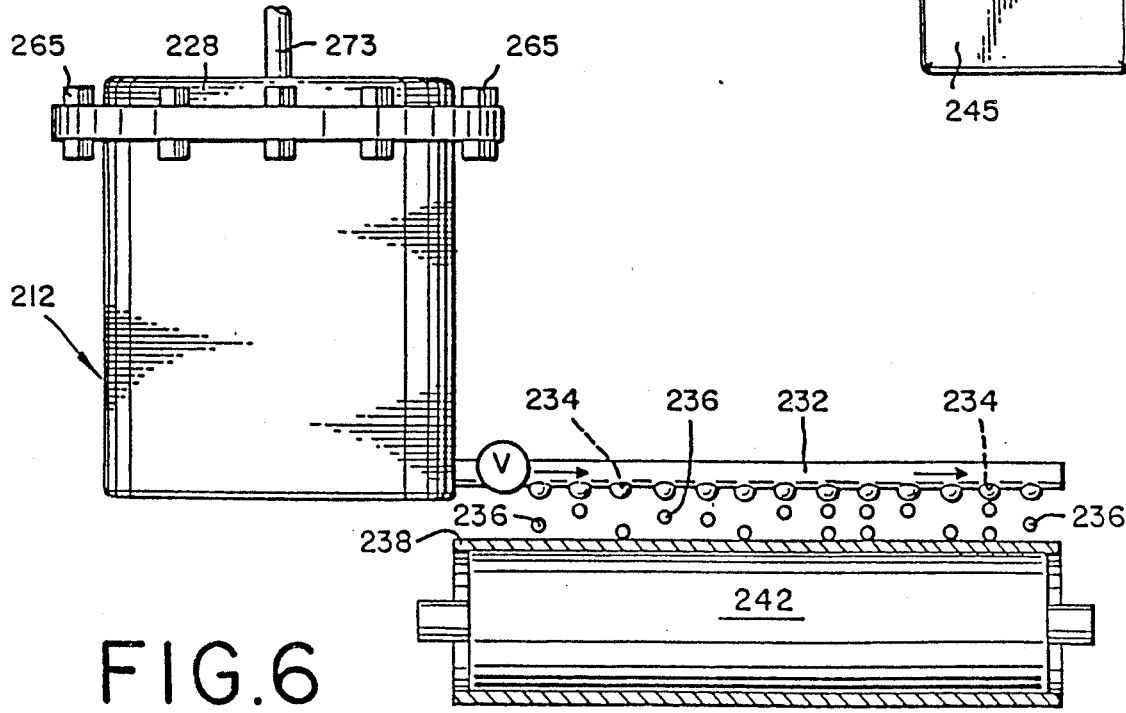

FIG. 6 is a cross sectional view taken along lines 6—6 of FIG. 5.

DETAILED DESCRIPTION OF THE DRAWINGS

Figure 1:
FIG. 1 is the GLC profile for the crude reaction product of Example I containing the compound having the structure.

FIG. 1 is the GLC profile for the crude reaction product of Example I containing the structure:

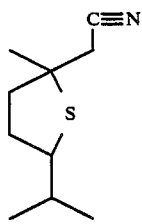

The peak indicated by reference numeral 10 is the peak for the compound having the structure:

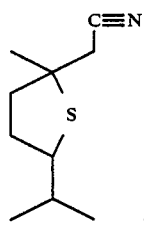

FIG. 2 is the GLC profile for fraction 6 of the distillation of the reaction product of Example I. (Conditions: SE-30 column programmed at 100°–220° C. at 8° C. per minute). The peak indicated by reference numeral 20 is the peak for the compound having the structure:

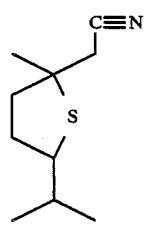

Referring to FIGS. 5 and 6; a thermoplastic polymer, e.g., polyethylene is heated to about 220°–250° C. in a container 212 of the kind illustrated in FIGS. 5 and 6. The formulation containing the tetrahydro-5-isopropyl-2-methyl-2-thiophene acetonitrile of our invention is then quickly added to the liquified thermoplastic polymer. The lid 228 is put in place and the agitating means 273 is actuated. The temperature is maintained at about 225° F. and the mixing is continued for about 5–15 minutes. The valve "V" is then opened to allow flow of the molten thermoplastic polymer enriched with the fragrance containing the tetrahydro-5-isopropyl-2-methyl-2-thiophene acetonitrile of our invention to exit through the orifices 234. The liquid falling through the orifices 234 solidifies almost instantaneously upon impact with moving cooled conveyor 238. The thermoplastic polymer beads or pellets 224 having pronounced aromas which are aesthetically pleasing are thus formed.

The conveyor 238 is moved using conveyor rollers 240 and 242. The vessel 212 is heated using heating coils 212A using power input supplies indicated by reference numerals 214, 216, 224, 222, 220 and 226. The solidified beads containing the tetrahydro-5-isopropyl-2-methyl-2-thiophene acetonitrile of our invention are indicated by 244 traveling into container 245 where they are used for subsequent processing. The conveyor is cooled using a cooling device indicated by reference numerals 248, 256, 215 and 254.

THE INVENTION

The invention relates to the compound defined according to the structure:

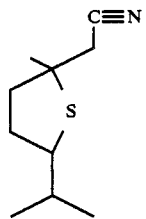

as well as uses thereof in augmenting or enhancing the aroma or taste of consumable materials. Such consumable materials are perfume compositions, perfumes, colognes, foodstuffs and chewing gums. This invention also relates to the process for preparing the compound having the structure by means of reacting geranonitrile, a mixture of compounds having the structures:

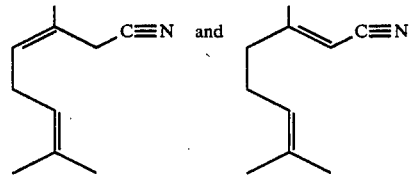

with thioacetic acid according to the reaction:

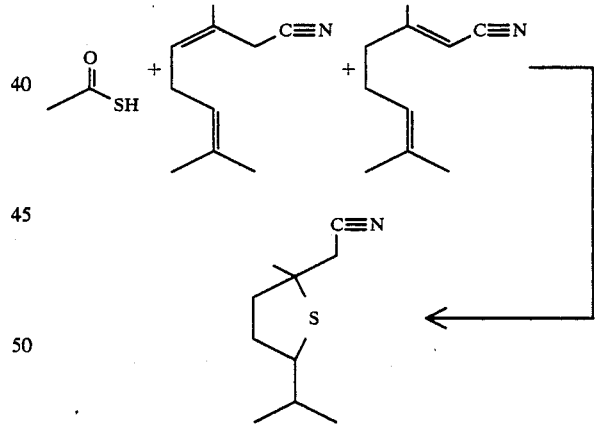

This reaction is carried out at a temperature of 60°–80° C. over a period of between about 1 and about 5 hours. The mole ratio of geranonitrile, the mixture of compounds having the structures:

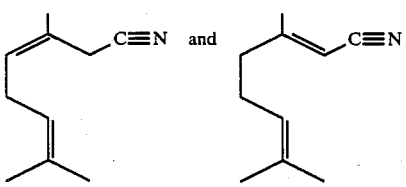

to thioacetic acid is between about 1:0.5 and about 0.5:1 with a slight excess of mixture of compounds having the structures:

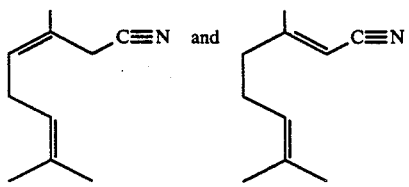

to thioacetic acid being preferred (e.g., 3:2.5).

At the end of the reaction the reaction mass is washed with base and fractionally distilled in order to recover the compound having the structure:

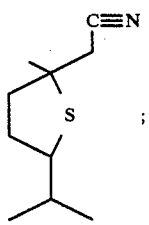

also shown as having the structure:

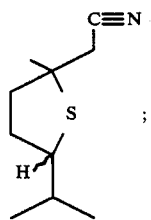

one or more isomers.

The compound having the structure:

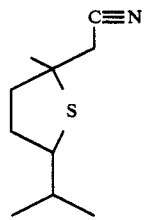

distills at 108° C. and 3 mm/Hg. pressure.

The compound having the structure:

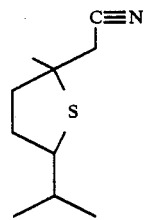

has a natural buchu leaf, tomato leaf, herbaceous, basil, minty and grapefruit-like aroma with natural "ontiga", tomato leaf, minty and grapefruit-like undertones from a fragrance standpoint. From a flavor standpoint the compound having the structure:

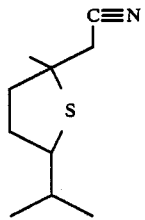

has a green, minty, grapefruit-like and nootkatone aroma and taste profile at 1 ppm.

The tetrahydro-5-isopropyl-2-methyl-2-thiophene acetonitrile of our invention having the structure:

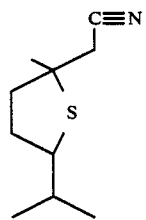

is useful as an olfactory agent and can be incorporated into a wide variety of compositions each of which will be enhanced or augmented by its natural buchu leaf, tomato leaf, herbaceous, basil, minty and grapefruit-like aroma with natural tomato leaf, minty and grapefruit-like undertones.

The tetrahydro-5-isopropyl-2-methyl-2-thiophene acetonitrile of our invention can be added to perfume compositions as a pure compound or can be added to mixtures of materials in fragrance imparting compositions to provide a desired fragrance character to a finished perfume material. The perfume and fragrance compositions obtained according to this invention are suitable in a wide variety of perfumed articles and can also be used to enhance, modify or reinforce natural fragrance materials. It will thus be appreciate that the tetrahydro-5-isopropyl-2-methyl-2-thiophene acetonitrile of our invention is useful as an olfactory agent and fragrance.

The term "perfume composition" is used herein to mean a mixture of compounds including, for example, natural essential oils, synthetic essential oils, alcohols, aldehydes, ketones, esters, lactones, nitriles (other than the nitrile of our invention) and frequently hydrocarbons which are admixed so that the combined odors of the individual components produce a pleasant or desired fragrance. Such perfume compositions usually contain (a) the main note or "bouquet" or foundation stone of the composition, (b) modifiers which round off and accompany the main note, (c) fixatives which include odorous substances which lend a particular note to the perfume throughout all stages of evaporation and substances which retard evaporation and (d) topnotes which are usually low-boiling, fresh-smelling materials. Such perfume compositions of our invention can be used in conjunction with carriers, vehicles, solvents, dispersants, emulsifiers, surface active agents, aerosol propellants and the like.

In perfume compositions, the olfactory components contribute their particular olfactory characteristics but the overall effect of the perfume composition will be the sum of the effect of each ingredient. This, the tetrahydro-5-isopropyl-2-methyl-2-thiophene acetonitrile of our invention can be used to alter, augment, modify or enhance the aroma characteristics of a perfume composition or a perfumed article, for example, by highlighting or moderating the olfactory reaction contributed by another ingredient of the composition.

The amount of the tetrahydro-5-isopropyl-2-methyl-2-thiophene acetonitrile of our invention which will be effective in perfume compositions depends upon many factors including the other ingredients, the amounts and the effects which are desired. It has been found that perfume compositions containing as much as 40% or as little as 0.005% by weight of the mixture of the tetrahydro-5-isopropyl-2-methyl-2-thiophene acetonitrile of this invention, or even less, can be used to impart a powerful, long-lasting, natural buchu leaf, tomato leaf, herbaceous, basil, minty and grapefruit-like aroma with natural "ontiga" tomato leaf, minty and grapefruit-like undertones to soaps, cosmetics and other products. The amount employed will depend upon considerations of cost, nature of the end product, the effect desired in the finished product and particular fragrance sought.

The tetrahydro-5-isopropyl-2-methyl-2-thiophene acetonitrile of our invention as disclosed herein can be used alone in a fragrance modifying composition or in a perfume composition as an olfactory component in detergents (e.g., anionic, cationic, nonionic or zwitterionic solid or liquid detergents, and soaps, space deodorants; perfumed plastics; perfume compositions; colognes, bath preparations such as bath oils, bath salts; hair preparations such as lacquers, brilliantines, pomades and shampoos; fabric softener compositions, fabric softener articles such as BOUNCE ® (manufactured by the Procter & Gamble Company of Cincinnati, Ohio), cosmetic preparations such as creams, powders, deodorants, hand lotions, sun screens, powders such as talcs, dusting powders, face powders and the like. When the tetrahydro-5-isopropyl-2-methyl-2-thiophene acetonitrile of our invention is used in perfumed articles such as the foregoing, it can be used in amounts of 0.01% or lower and generally it is preferred not to use more than about 2% in the finished perfumed article since the use of too much will tend to unbalance the total aroma and will needlessly raise the cost of the article. Thus, in summary, in perfumed articles, the tetrahydro-5-isopropyl-2-methyl-2-thiophene acetonitrile of our invention having the structure:

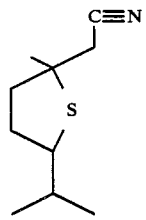

may be used in the range of from about 0.01% up to about 2.0%.

When the tetrahydro-5-isopropyl-2-methyl-2-thiophene acetonitrile of our invention having the structure:

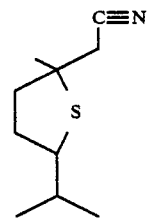

is used as a food flavor adjuvant, or is used to augment or enhance the flavor or aroma characteristics of foodstuffs, the nature of the co-ingredients included with said tetrahydro-5-isopropyl-2-methyl-2-thiophene acetonitrile of our invention in formulating the product composition will also to augment the organoleptic characteristics of the ultimate foodstuff treated therewith.

As used herein in regard to flavors, the term "augment" in its various forms means "supplying or imparting flavor, character or note to otherwise bland, relatively tasteless substances or augmenting the existing flavor characteristics wherein natural flavor is deficient in some regard or supplementing the existing flavor impression to modify its quality, character or taste".

As used herein in regard to food flavors, the term "enhance" is used to mean the intensification of a flavor or aroma characteristic or note without the modification of the quality thereof. Thus "enhancement" of a flavor or aroma means that the enhancement agent does not add any additional flavor note.

As used herein the term "foodstuff" includes both solids and liquids and ingestible materials or chewable but non-ingestible materials such as chewing gum. Such materials usually do, but need not have nuritional value. Thus, foodstuffs include soups, convenience foods, beverages, gelatin desserts, dairy products, candies, vegetables, cereals, soft drinks, snacks and the like.

Substances suitable for use herein as co-ingredients or flavoring adjuvants are well known in the art for such use, being extensively described in the relevant literature. Apart from the requirements that any such materials be organoleptically compatible with the tetrahydro-5-isopropyl-2-methyl-2-thiophene acetonitrile of our invention having the structure:

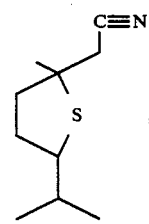

non-reactive with the tetrahydro-5-isopropyl-2-methyl-2-thiophene acetonitrile of our invention and "ingestibly acceptable" and thus, non-toxic or otherwise non-deleterious, nothing particularly critical resides in the selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3 tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skin milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, beta,beta-dimethylacrolein, n-hexanal, 2-hexenal, cis-3-hexenal, 2-heptanal, 4-(p-hydroxyphenyl)-2-butanone, alpha-ionone, beta-ionone, methyl-3-butanone, 2-pentanone, 2-pentenal and propanal; alcohols such as 1-butanal, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmin absolute, rose absolute, orris absolute, lemon essential oil, Bulgarian rose, yara yara, natural raspberry oil and vanilla; lactones; sulfides, e.g., methyl sulfide and other materials such as maltol, pulegone mercaptan, alpha-phellandrene, ethyl maltol, 2,2,4,4,6,6-hexamethyl-S-trithiane, acetoin and acetals, (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, be capable of providing an environment in which the tetrahydro-5-isopropyl-2-methyl-2-thiophene acetonitrile of our invention can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of the tetrahydro-5-isopropyl-2-methyl-2-thiophene acetonitrile of our invention employed in a particular instance can vary over a relatively wide range whereby to its desired organoleptic effects having reference to the nature of the product are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter the organoleptic characteristics of the parent composition, whether foodstuff per se of flavoring composition.

The use of insufficient quantities of the tetrahydro-5-isopropyl-2-methyl-2-thiophene acetonitrile of our invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of the tetrahydro-5-isopropyl-2-methyl-2-thiophene acetonitrile of our invention ranging from a small but effective amount, e.g., about 0.1 parts per million up to about 50 parts per million by weight based on total composition (more preferably, from about 0.2 ppm up to about 10 ppm) are suitable. Concentrations in excess of the maximum quantity stated are not normally recommended since they fail to prove commensurate with enhancement of organoleptic properties. In those instance wherein the tetrahydro-5-isopropyl-2-methyl-2-thiophene acetonitrile of our invention are added to the foodstuff as an integral component of a flavoring composition it is, of course, essential that the total quantity of flavoring composition employed be sufficient to yield an effective tetrahydro-5-isopropyl-2-methyl-2-thiophene acetonitrile of our invention in the foodstuff product.

Food flavoring compositions prepared in accordance with the present invention preferably contain the tetrahydro-5-isopropyl-2-methyl-2-thiophene acetonitrile of our invention in concentrations ranging from about 0.1% up to about 15% by weight based on the total weight of said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the tetrahydro-5-isopropyl-2-methyl-2-thiophene acetonitrile of our invention with, for example, gum arabic, gum tragacanth, carageenan and the like, and thereafter spray-drying the resultant mixture whereby to obtain the particular solid product. Pre-prepared flavor mixed in powder form, e.g., a fruit flavored powder mix, is obtained by mixing the dried solid components, e.g., starch, sugar and the like, and the tetrahydro-5-isopropyl-2-methyl-2-thiophene acetonitrile of our invention in a dry blender until the requisite degree of uniformity is achieved.

It is presently preferred to combine with the tetrahydro-5-isopropyl-2-methyl-2-thiophene acetonitrile of our invention the following adjuvants:
p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl perlargonate;
Methyl anthranilate;
Isoamyl acetate;
Isobutyl acetate;
Alpha-ionone;
Ethyl butyrate;
Acetic acid;
Gamma-undecalactone;
Naphthyl ethyl ether;
Diacetyl;
Ethyl acetate;
Anethole;
Isoamyl butyrate;
Cis-3-hexenol-1;
2-Methyl-2-pentenoic acid;
Elemecine(4-allyl-1,2,6-trimethoxy benzene);
Isoelemecine(4-propenyl-1,2,6-trimethoxybenzene);
2-(4-Hydroxy-4-methylpentyl)norbornadiene prepared according to U.S. application for patent, Ser. No. 461,703 filed on Apr. 17, 1974, now U.S. Pat. No. 3,886,289;
Natural blackcurrent juice;
Buchu leaf oil;
Alpha-phellandrene;
Cis-3-hexen-1-ol;
Terpinenol-4;
Ethyl maltol;
Methyl benzoate;
Benzaldehyde;
Coriander oil;
Alpha-ionone;
Ethyl heptanoate;
Ethyl anthranilate;
Cinnamic alcohol;
Amyl valerinate;
Cinnamyl propionate;
Rhodinyl acetate;
Methyl beta-hydroxy butyrate;
Ethyl beta-hydroxy butyrate;
2-Phenyl-3-carboethoxyfuran;
Cyclohexyl disulfide;
Grapefruit oil
Nootkatone;
Bergamot oil;
Citral;
Amyl alcohol;
5-Phenyl-4-pentenal;
5-Phenyl-2-pentenal;
Allyl caproate;
2-(n-Pentyl)thiazole;
2-(i-Butyl)thiazole;
2-(i-Propyl)thiazole;
2-(n-propyl)thiazole;
2-Phenyl-4-pentenal;
2-Phenyl-4-pentenaldimethylacetal;
Methional;
4-Methylthiobutanal;
2-Ethyl-3-acetylpyrazine;
Tetramethyl pyrazine;
2-Methyl pyrazine;
Trans-2-hexenal;
Hydrolyzed vegetable protein;
Monosodium glutamate;
Dimethyl disulfide;
Methyl propyl disulfide;
Methyl propenyl disulfide;
Methyl allyl disulfide;
Allyl propyl disulfide;
Propyl propenyl disulfide;
Dipropyl disulfide;
Diallyl disulfide;
Propyl propenyl trisulfide;
Thiopropanal-S-oxide;
Thiobutanal-S-oxide;
Thioethanal-S-oxide;
Thiohexanal-S-oxide; and
Propyl propene thiosulfonate.

The following Example I is given to illustrate a method of preparing the tetrahydro-5-isopropyl-2-methyl-2-thiophene acetonitrile of our invention. The examples following Example II set forth methods whereby the tetrahydro-5-isopropyl-2-methyl-2-thiophene acetonitrile of our invention is utilized for its organoleptic properties.

It will be understood that these examples are illustrative and the invention is not to be considered as restricted thereto except as indicated in the appended claims.

EXAMPLE I

PREPARATION OF TETRAHYDRO-5-ISOPROPYL-2-METHYL-2-THIOPHENE ACETONITRILE

Reaction

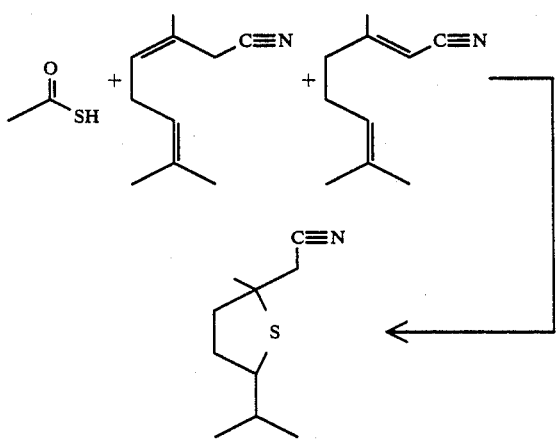

Into a 1 liter reaction vessel equipped with thermometer, stirrer, condenser and heating mantle is placed 455.0 grams (3.0 moles) of geranonitrile, a mixture of compounds having the structures:

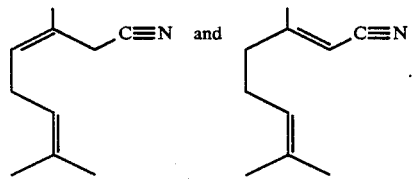

The geranonitrile is heated with stirring to 65° C. Dropwise, over a period of 60 minutes, while maintaining the reaction temperature at 65° C., 190.0 grams (2.5 moles) of thioacetic acid is added to the reaction mass.

The reaction mass is then stirred at 65°-70° C. of one hour. The reaction mass is then heated and maintained at 70°-75° C. for a period of 1.25 hours.

The reaction mass is the cooled and 200 cc toluene is added thereto. The organic layer is separated from the aqueous phase and the organic layer is washed with one 200 cc portion of 20% aqueous sodium hydroxide. The resulting washed product is then distilled on a 6" stone packed column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 90/100 | 120/125 | 3.0/3.0 | 15.0 |
| 2 | 100 | 135 | 3.5 | 15.0 |
| 3 | 105 | 145 | 3.5 | 40.0 |
| 4 | 105 | 160 | 3.5 | 50.0 |
| 5 | 108 | 175 | 3.5 | 60.0 |
| 6 | 108 | 177 | 3.0 | 30.0 |
| 7 | 108 | 179 | 3.0 | 45.0 |
| 8 | 108 | 181 | 3.0 | 20.0 |

The resulting distillation product is then bulked and redistilled on a spinning band column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 90/95 | 110/141 | 2.5/2.5 | 10.0 |
| 2 | 95 | 150 | 2.5 | 30.0 |
| 3 | 95 | 150 | 2.5 | 5.0 |
| 4 | 108 | 158 | 2.5 | 30.0 |
| 5 | 108 | 165 | 2.5 | 24.0 |
| 6 | 108 | 165 | 2.5 | 29.0 |
| 7 | 108 | 170 | 2.5 | 27.0 |
| 8 | 108 | 195 | 2.8 | 36.0 |

FIG. 1 is the GLC profile for the crude reaction product. The peak indicated by reference numeral 10 is the peak for the compound having the structure:

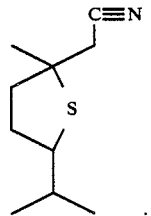

FIG. 2 is the GLC profile for fraction 6 of the second distillation (Conditions: SE-30 column programmed at 100°-220° C. at 8° C. per minute). The peak indicated by reference numeral 20 is the peak for the compound having the structure:

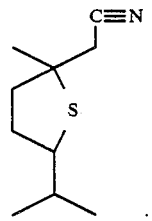

FIG. 3 is the NMR spectrum for the compound having the structure:

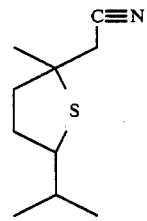

FIG. 4 is IR spectrum for the compound having the structure:

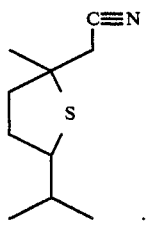

The compound having the structure:

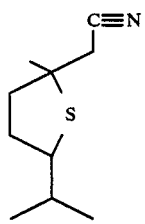

has a natural natural buchu leaf, tomato leaf, herbaceous, basil, minty and grapefruit-like aroma with natural "ontiga", tomato leaf, minty and grapefruit-like undertones from a fragrance standpoint.

From a flavor standpoint the compound having the structure:

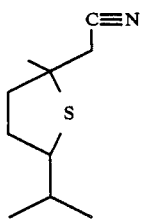

has a green, minty, grapefruit-like and nootkatone-like aroma and taste profile.

EXAMPLE II(A)

IMPREGNATED PLASTICS AND AIR FRESHENERS

Scented polyethylene pellets having pronounced natural buchu leaf, tomato leaf, herbaceous, basil, minty and grapefruit-like aromas with natural "ontiga" tomato leaf, minty and grapefruit-like undertones are prepared as follows:

75 Pounds of polyethylene having a melting point of about 220° F. is heated to about 230° F. in a container of the kind illustrated in FIGS. 5 and 6. 12.5 Pounds of tetrahydro-5-isopropyl-2-methyl-2-thiophene acetonitrile having the structure:

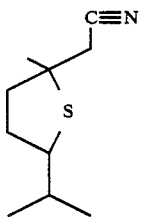

prepared according to Example I, supra, are then quickly added to the liquified polyethylene. The lid 228 is put in place and the agitating means 273 are actuated. The temperature is maintained at about 225° F. and the mixing is continued for about 15 minutes. The valve "V" is then opened to allow flow of the molten polyethylene enriched with the tetrahydro-5-isopropyl-2-methyl-2-thiophene acetonitrile containing material through the orifices 234 (whereby such material exits through orifices 234). The liquid falling through the orifices 234 solidifies almost instantaneously upon impact with the moving cooled conveyor 238. Polyethylene beads or pellets 224 having a pronounced aroma as set forth above are thus formed. These pellets may be called "master pellets".

50 Pounds of the aroma-containing "master pellets" are then added to 1000 pounds of unscented and untreated polyethylene powder and the mass is heated to the liquid state. The liquid is molded into thin sheets or films. The thin sheets or films have pronounced aromas as set forth, supra. The sheets or films are cut into strips ¼" in width×3" in length and employed in standard air freshening apparatus.

On operation of the standard air freshening apparatus is a room air freshener, after 4 minutes, the room has an aesthetically pleasing aroma as set forth, supra.

EXAMPLE II(B)

TREATED PLASTICS AND AIR FRESHENER

100 Pounds of polypropylene are heated to about 300° F. 15 Pounds of tetrahydro-5-isopropyl-2-methyl-2-thiophene acetonitrile prepared according to Example I are added to the liquified polypropylene. The procedure is carried out in the apparatus shown in FIGS. 5 and 6. After mixing for about 8 minutes, the valve "V" is opened to allow the exit of polypropylene mixture which has been treated with the tetrahydro-5-isopropyl-2-methyl-2-thiophene acetonitrile whereby solid pellets having pronounced aromas described as "natural buchu leaf, tomato leaf, herbaceous, basil, minty and grapefruit-like with natural "ontiga", tomato leaf, minty and grapefruit-like undertones" are formed on the conveyor. The pellets thus obtained are then admixed with about 20 times their weight of unscented polypropylene and untreated polypropylene and the mixture is heated and molded into "spaghetti" tows. The "spaghetti" tows are cut into small cylinders approximately 0.1 inches in length×0.2 inches in diameter. The cylinders have strong and pleasant aromas as described, supra.

The cylinders are used in standard air freshening apparatus to produce aesthetically pleasing aromas as set forth, supra, with no foul odors in environments surrounding the air freshener apparatus.

A portion of the cylinders are ground into small particles to be used in the deodorant stick of Example II(C).

EXAMPLE II(C)

DEODORANT STICK

A deodorant stick composition is prepared containing the following materials:

| Ingredients | Parts by Weight |
| --- | --- |
| Propylene Glycol | 65.00 |
| Sodium stearate | 7.00 |
| Distilled water | 23.75 |

-continued

| Ingredients | Parts by Weight |
|---|---|
| IRGSAN ® DP-300 (2,4,4-trichloro-2'-hydroxy diphenyl ether, manufactured by the Ciba Geigy Chemical Company and the trademark of the Ciba Geigy Chemical Company of Hastings on Hudson, New York) | 0.25 |
| Ground polymer containing tetrahydro-5-isopropyl-2-methyl-2-thiophene acetonitrile produced according to Example II(B), supra. | 4.00 |

The ingredients are combined without the ground polymer and are heated to 75° C. These ingredients are mixed and continued to be heated until the sodium stearate has dissolved. The resulting mixture is cooled to 40° C. and the ground fragrance-containing polymer is added and mixed at 40° C. until a suspension is formed. The resulting suspension is cooled and formed into sticks and the deodorant sticks exhibit a pleasant fresh green aroma when utilized in the axillary areas of a human being.

EXAMPLE III

GRAPEFRUIT FLAVOR FORMULATION

The following formulation is prepared:

| Ingredients | Parts by weight Example III(A) | Parts by weight Example III(B) |
|---|---|---|
| Grapefruit oil | 92.0 | 92.0 |
| Bergamot oil | 2.0 | 2.0 |
| Citral | 3.0 | 3.0 |
| n-Amyl alcohol | 1.0 | 1.0 |
| Ethyl acetate | 1.0 | 1.0 |
| 2-Methyl-4-phenyl-1-pentanol produced according to U.S. Pat. No. 4,632,831 | 1.5 | 0.0 |
| 2-Methyl-4-phenyl-1-pentanol acetate produced according to U.S. Pat. No. 4,632,831 | 0.0 | 1.8 |
| Tetrahydro-5-isopropyl-2-methyl-2-thiophene acetonitrile produced according to Example I, supra | 2.0 | 2.0 |

When the above grapefruit formulations are added to water at the rate of 1%, an excellent grapefruit drink is prepared. The tetrahydro-5-isopropyl-2-methyl-2-thiophene acetonitrile of our invention gives a minty, natural green nuance to the above two formulations thereby rendering them more "natural-like". Furthermore, the formulation are both "nootkatone" like with aesthetically pleasing red grapefruit notes.

When the above formulations are modified by adding to them 1.5 parts by weight of any of the following ingredients a yet more natural grapefruit peel aroma and taste is imparted thereto:
(1,3-diethylacetonyl)(1,3-diisopropylacetonyl)sulfide;
3-methyl-thio-4-heptanone;
3-propyl-thio-4-heptanone;
3-(methallythio)-2,6-dimethyl-4-heptanone;
3-crotylthio-2,6-dimethyl-4-heptanone; and
3-allylthio-2,6-dimethyl-4-heptanone.

EXAMPLE IV (A.) The following concentrate is prepared:

| Ingredients | Parts by Weight |
|---|---|
| Geraniol | 1.00 |
| Ethyl methyl phenyl glycidate | 3.50 |
| Nootkatone | 5.00 |
| Ethyl pelargonate | 5.00 |
| Isoamyl acetate | 4.00 |
| Vanillin | 2.00 |
| Isobutyl-2-methyl-pentenoate | 3.00 |
| 2-Methyl-4-phenyl-1-pentanol | 1.00 |
| 2-Methyl-4-phenyl-1-pentanol acetate | 1.13 |
| Tetrahydro-5-isopropyl-2-methyl-2-thiophene acetonitrile | 1.00 |

(B.) One volume of the concentrate prepared in Part "A", supra, is dissolved in four volumes of propylene glycol and the mixture is added to a hard candy melt at the rate of 1.5 ounces of the concentrate solution per 100 pounds of melt. After the finished candy has been produced, it is found to have an excellent grapefruit flavor. When the candy is compared with candy made under the same conditions but without the tetrahydro-5-isopropyl-2-methyl-2-thiophene acetonitrile of our invention, it is found to have an inferior grapefruit flavor. Indeed, the grapefruit flavor used with the tetrahydro-5-isopropyl-2-methyl-2-thiophene acetonitrile of our invention is markedly superior than without the tetrahydro-5-isopropyl-2-methyl-2-thiophene acetonitrile of our invention.

EXAMPLE V

A. POWDER FLAVOR FORMULATION

Twenty grams of the flavor formulation of Example III is emulsified in a solution containing 300 grams gum acacia and 700 grams of water. The emulsion is spray-dried with a Bowen Lab Model Drier utilizing 260 c.f.m. of air with an inlet temperature of 500° F., an outlet temperature of 200° F. and a wheel speed of 50,000 rpm.

B. SUSTAINED RELEASE FLAVOR

The following mixture is prepared:

| Ingredients | Parts by Weight |
|---|---|
| Liquid grapefruit flavor of Example III | 20 |
| Propylene glycol | 9 |
| CAB-O-SIL ® M-5 (Brand of silica produced by the Cabot Corporation of 125 High Street, Boston, Mass. 02110); | 5 |
| Physical Properties | |
| Surface area: 200 m₂/gram Nominal particle size: 0.012 microns Density: 2.3 lbs./cu.ft. | |

The CAB-O-SIL ® is dispersed in the liquid grapefruit flavor composition of Example III with vigorous stirring thereby resulting in a viscous liquid. 71 Parts by weight of the powder flavor composition of Part "A", supra, is then blended into said viscous liquid with stirring at 25° C. for a period of thirty minutes resulting in a dry, free-flowing, sustained release grapefruit flavored powder.

EXAMPLE VI

Ten parts by weight of 50 Bloom pigskin gelatin is added to ninety parts by weight of water at a temperature of 150° C. The mixture is agitated until the gelatin is completely dissolved and the solution is cooled to 120° F. Twenty parts by weight of the liquid grapefruit flavor composition of Example III is added to the solution which is then homogenized to form an emulsion having a particle size typically in the range of 5–40 microns. The material is kept at 120° F. under which conditions the gelatin will not jell.

Coacervation is induced by adding slowly and uniformly forty parts by weight of a 20% aqueous solution of sodium sulfate. During coacervation, the gelatin molecules are deposited uniformly about each oil droplet as a nucleus.

Gelatin is effected by pouring the heated coacervate mixture into 1,000 parts by weight of 7% aqueous solution of sodium sulfate at 65° F. The resulting jelled coacervate may be filtered and washed with water at temperatures below the melting point of gelatin to remove the salt.

Hardening of the filtered cake, in this example, is effected by washing with 200 parts by weight of 37% solution of formaldehyde in water. The cake is then washed to remove residual formaldehyde.

EXAMPLE VII

CHEWING GUM

One hundred parts by weight of chicle are mixed with four parts by weight of the flavor prepared in accordance with Example V. Three hundred parts of sucrose and one hundred parts of corn syrup are added. Mixing is effected in a ribbon blender with jacketed walls of the type manufactured by the Baker Perkins Company.

The resultant chewing gum blend is then manufactured into strips one inch in width and 0.1 inches in thickness. The strips are cut into lengths of three inches each. On chewing, the chewing gum has a pleasant long-lasting grapefruit flavor.

EXAMPLE VIII

CHEWING GUM

One hundred parts by weight of chicle are mixed with eighteen parts by weight of the flavor prepared in accordance with Example VI. Three hundred parts of sucrose and one hundred parts of corn syrup are then added. Mixing is effected in a ribbon blender with jacketed walls of the type manufactured by the Baker Perkins Company.

The resultant chewing gum blend is then manufactured into strips one inch in width and 0.1 inches in thickness. The strips are cut into lengths of three inches each. On chewing, the chewing gum has a pleasant, long-lasting grapefruit flavor.

EXAMPLE IX

TOOTHPASTE FORMULATION

The following separate groups of ingredients are prepared:

| Parts by Weight | Ingredient |
|---|---|
| Group "A" | |
| 30.200 | Glycerine |
| 15.325 | Distilled water |
| .100 | Sodium benzoate |
| .125 | Saccharin sodium |
| .400 | Stannous flurode |
| Group "B" | |
| 12.500 | Calcium carbonate |
| 37.200 | Dicalcium phosphate dihydrate |
| Group "C" | |
| 2.000 | Sodium n-lauroyl sarcosinate (foaming agent) |
| Group "D" | |
| 1.200 | Flavor material of Example V |

Procedure
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly, the sodium n-lauroyl sarcosinate.
5. The resultant slurry is then blended for one hour. The completed paste is then tranferred to a three roller mill and then homogenized and finally tubed.

The resulting toothpaste, when used in a normal toothbrushing procedure, yields a pleasant grapefruit flavor of constant strong intensity throughout said procedure (1–1.5 minutes).

EXAMPLE X

CHEWABLE VITAMIN TABLETS

The flavor material produced according to the process of Example VI is added to a chewable vitamin tablet formulation at the rate of ten grams per kilogram which chewable vitamin tablet formulation is prepared as follows:

In a Hobart mixer, the following materials are blended to homogeneity:

| Ingredients | Grams/1000 Tablets |
|---|---|
| Vitamin C (ascorbic acid) as ascorbic acid-sodium ascorbate mixture 1:1 | 70.110 |
| Vitamin $B_1$ (thiamine mononitrate) as ROCOAT ® thiamine mononitrate 33⅓% (Hoffman LaRoche) | 4.000 |
| Vitamin $B_2$ (riboflavin) as ROCOAT ® riboflavin 33⅓% | 5.000 |
| Vitamin $B_6$ (pyridoxine hydrochloride) as ROCOAT ® phridoxine hydrochloride 33⅓% | 4.000 |
| Niacinamide as ROCOAT ® niacinamide 33⅓% | 33.000 |
| Calcium pantothenate | 11.500 |
| Vitamin $B_{12}$ (cyanocobalamin) as Merck 0.1% in gelatin | 3.500 |
| Vitamin E (dl-alpha tocopheryl acetate) as dry Vitamin E acetate 33⅓% | 6.600 |
| d-Biotin | 0.044 |
| Flavor of Example VI | (as indicated above) |
| Certified lake color | 5.000 |
| Sweetener, sodium saccharin | 1.000 |
| Magnesium stearate lubricant | 10.000 |
| Mannitol q.s. to make | 500.000 |

Preliminary tablets are prepared by slugging with flat-faced punches and grinding the slugs to 14 mesh.

13.5 Grams dry Vitamin A acetate and 0.6 grams Vitamin D are then added as beadlets. The entire blend is then compressed using concave punches at 0.5 grams each.

Chewing of the resultant tablets yields a pleasant, long-lasting, consistently strong grapefruit flavor for a period of 12 minutes.

EXAMPLE XI

HERBAL PERFUME FORMULATION

The following mixtures are prepared:

| Ingredients | Parts by Weight | |
|---|---|---|
| | Example XI(A) | Example XI(B) |
| Oakmoss absolute (50% in diethyl phthalate) | 20 | 20 |
| Alpha-methyl-3,4,methylene-dioxyhydrocinnamic aldehyde | 10 | 10 |
| Methyl dihydrojasmonate | 100 | 100 |
| Coumarin | 20 | 20 |
| Musk ketone | 80 | 80 |
| Isocyclocitral (10% in diethyl phthalate) | 10 | 10 |
| Galbanum oil (10% in diethyl phthalate) | 6 | 6 |
| Rosemary oil | 10 | 10 |
| Pine needle oil | 60 | 60 |
| Fir balsam absolute (10% in diethyl phthalate) | 10 | 10 |
| Bergamot oil | 60 | 60 |
| Lemon oil | 14 | 14 |
| Benzyl acetate | 468 | 468 |
| Linalool | 80 | 80 |
| Indole (10% in diethyl phthalate) | 6 | 6 |
| Undecalactone (10% in diethyl phthalate) | 12 | 12 |
| 2-methyl-4-phenyl-1-pentanol (produced according to U.S. Letters Pat. No. 4,632,831) | 12 | 0 |
| 2-methyl-4-phenyl-1-pentanol acetate (produced according to U.S. Letters Pat. No. 4,632,831) | 0 | 20 |
| Tetrahydro-5-isopropyl-2-methyl-2-thiopene acetonitrile produced according to Example I, supra. | 10 | 5 |

The addition to this herbal formulation of the tetrahydro-5-isopropyl-2-methyl-2-thiophene acetonitrile imparts to this herbal formulation an excellent natural buchu leaf, tomato leaf, herbaceous, basil, minty and grapefruit-like topnotes, with natural "ontiga", tomato leaf, minty and grapefruit-like undertones. Accordingly, the formulations can be described as "herbaceous with natural buchu leaf, tomato leaf, herbaceous, basil, minty and grapefruit-like topnotes and natural "ontiga", tomato leaf, minty and grapefruit-like undertones".

EXAMPLE XII

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
|---|---|
| Tetrahydro-5-isopropyl-2-methyl-2-thiopene acetonitrile produced according to Example I. | A natural buchu leaf, tomato leaf, herbaceous, basil, minty and grapefruit-like aroma profile with natural "ontiga", tomato leaf, minty and grapefruit-like undertones. |
| Perfume formulations to Example XI. | Herbaceous with natural buchu lead, tomato leaf, herbaceous, basil, minty and grapefruit-like topnotes and natural "ontiga", tomato leaf, minty and grapefruit-like undertones. |

EXAMPLE XIII

PERFUMED LIUQID DETERGENTS

Concentrated liquid detergents (Lysine salt of n-dodecylbenzene sulfonic acid as more specifically described in U.S. Pat. No. 3,948,818 issued Apr. 6, 1976 incorporated by reference herein) with aroma nuances as set forth in Table I of Example XII are prepared containing 0.10%, 0.15%, 0.20%, 0.25%, 0.30% and 0.35% of the substance set forth in Table I of Example XII. They are prepared by adding and homogeneously mixing the appropriate quantity of substance set forth in Table I of Example XII in the liquid detergent. The detergents all possess excellent aromas as set forth in Table I of Example XII, the intensity increasing with greater concentrations of substance as set forth in Table I of Example XII.

EXAMPLE XIV

PREPARATION OF COLOGNES AND HANDKERCHIEF PERFUMES

Compositions as set forth in Table I of Example XII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definite fragrances as set forth in Table I of Example XII are imparted to the colognes and to the handkerchief perfumes at all levels indicated.

EXAMPLE XVI

PREPARATION OF SOAP COMPOSITIONS

One hundred grams of soap chips (per sample) (IVORY ®, produced by the Procter & Gamble Company of Cincinnati, Ohio), are each mixed with one gram samples of substances as set forth in Table I of Example XII until homogeneous compositions are obtained. In each of the cases, the homogeneous compositions are heated under eight atmospheres pressure at 180° C. for a period of three hours and the resulting liquids are placed into soap molds. The resulting soap cakes, on cooling, manifest aromas as set forth in Table I of Example XII.

EXAMPLE XVII

PREPARATION OF SOLID DETERGENT COMPOSITIONS

Detergents are prepared using the following ingredients according to Example I of Canadian Patent No. 1,007,948 (incorporated by reference herein):

| Ingredient | Percent by Weight |
| --- | --- |
| "NEODOL ® 45-11" (a $C_{14}$-$C_{15}$ alcohol ethoxylanted with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example XII. Each of the detergent samples has an excellent aroma as indicated in Table I of Example XII.

EXAMPLE XVIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
1. A water "dissolvable" paper ("Dissolvo Paper"); and
2. Adogen 448 (m.p. about 140° F.) as the substrate coating; and pH3. An outer coating having the following formulation (m.p. about 150° F.):

57% $C_{20-22}$ HAPS
22% isopropyl alcohol
20% antistatic agent
1% of one of the substances as set forth in Table I of Example XII.

Fabric softening compositions prepared according to Example I at column 15 of U.S. Pat. No. 3,632,396 having aroma characteristics as set forth in Table I of Example XII, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example XII is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table I of Example XII, supra.

EXAMPLE XIX

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of the polymer is dissolved in the alcohol. The following ingredients are added to the PVP/VA alcoholic solution:

| | Weight Percent |
| --- | --- |
| Dioctyl sebacate | 0.05 |
| Benzyl alcohol | 0.10 |
| Dow Corning 473 fluid (prepared by the Dow Corning Corporation) | 0.10 |
| TWEEN ® °surfactant (prepared by ICI America Corporation) | 0.03 |
| One of the perfumery substances as set forth in Table I of Example XII, supra | 0.10 |

The perfuming substances as set forth in Table I of Example XII add aroma characteristics as set forth in Table I of Example XII which are rather intense and aesthetically pleasing to the users of the soft-feel, good-hold pump hair sprays.

EXAMPLE XX

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol disterate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, N.Y.) (5.0 weight percent) is admixed with 0.1 weight percent sodium sulfite and 1.4 percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table I of Example XII is added to the mixture. The resulting mixture is cooled to 40° C. and blending is carried out for an additional one hour in each case. At the end of this blending period, the resulting material has a pleasant fragrance as indicated in Table I of Example XII.

What is claimed is:
1. A process for augmenting or enhancing the grapefruit aroma or taste of a foodstuff or chewing gum comprising the step of adding to said foodstuff or chewing gum from about 0.1 ppm up to about 50 ppm by weight based on the total weight of said foodstuff or chewing gum of tetrahydro-5-isopropyl-2-methyl-2-thiophene acetonitrile having the structure:

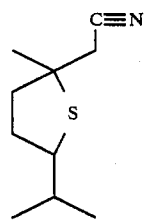

* * * * *